United States Patent
Selton

(10) Patent No.: US 10,376,418 B1
(45) Date of Patent: Aug. 13, 2019

(54) CONTINUOUS CONFIGURABLE ADHESIVE BANDAGE

(71) Applicant: Daniel E Selton, Alpharetta, GA (US)

(72) Inventor: Daniel E Selton, Alpharetta, GA (US)

(\*) Notice: Subject to any disclaimer, the term of this patent is extended or adjusted under 35 U.S.C. 154(b) by 0 days.

(21) Appl. No.: 15/933,202

(22) Filed: Mar. 22, 2018

(51) Int. Cl.
*A61F 13/02* (2006.01)
*A61F 13/00* (2006.01)
*A61L 15/58* (2006.01)

(52) U.S. Cl.
CPC .... *A61F 13/0266* (2013.01); *A61F 13/00063* (2013.01); *A61F 13/024* (2013.01); *A61F 13/0253* (2013.01); *A61F 13/0289* (2013.01); *A61L 15/58* (2013.01); *A61F 13/0206* (2013.01)

(58) Field of Classification Search
CPC .. A61F 13/02; A61F 13/0259; A61F 13/0253; A61F 13/022; A61F 13/0289; A61F 2013/00604; A61F 2013/00812; A61F 13/0266; A61F 13/024; A61F 13/00085
USPC ........... 602/1, 42, 52, 57; 424/445, 448, 449
See application file for complete search history.

(56) References Cited

U.S. PATENT DOCUMENTS

| | | | | |
|---|---|---|---|---|
| 5,501,661 A | * | 3/1996 | Cartmell | A61F 13/023 424/443 |
| 5,695,456 A | * | 12/1997 | Cartmell | A61B 17/085 206/409 |
| 2006/0161088 A1 | * | 7/2006 | Voetsch | A61F 15/002 602/43 |
| 2010/0298747 A1 | * | 11/2010 | Quinn | A61F 5/40 602/1 |

\* cited by examiner

*Primary Examiner* — Ophelia A Hawthorne
*Assistant Examiner* — Caitlin A Carreiro
(74) *Attorney, Agent, or Firm* — Gerald Boss

(57) ABSTRACT

A bandage includes a body and an adhesive layer. An attachment portion is defined by exposing the adhesive layer. The bandage includes a first removable dressing component having a predetermined length and width carried by the adhesive layer disposed over the central axis of the body. A second removable dressing component having a predetermined length and width is also carried by the adhesive layer. The respective widths of the first and second removable dressing components being less than the width of the body enabling a side edge attachment portion to be defined proximate the side edges of the body and wherein the removal of the first removable dressing component exposes the adhesive layer defining an end attachment portion of the bandage.

19 Claims, 5 Drawing Sheets

CONTINUOUS CONFIGURABLE ADHESIVE BANDAGE

TECHNICAL FIELD

This invention relates generally to the field of wound care and more particularly to a wound care device consisting of a continuous configurable adhesive bandage which may be customized to cover and protect a wound of a desired length.

BACKGROUND OF THE INVENTION

Wound dressings are applied to wounds to protect them from the environment enabling them to heal. Such dressings generally consist of a gauze which is wrapped or applied to the wound. The gauze may have therapeutic additives which enable the wound to heal in a more efficient or healthy manner. The wound dressing must be maintained in place to protect the underlying wound. For this reason, the wound dressing is typically secured.

One typical wound dressing is an adhesive bandage type. An adhesive bandage type includes a strip of material, typically a plastic outer layer with an adhesive on the underside of the plastic outer layer. A gauze pad is disposed underneath the plastic outer layer on the same side as the adhesive. A removeable covering sheet covers the gauze pad and adhesive. Typically, the entire bandage is enclosed in a package that maintains the sterility of the bandage until opened. The bandage is then applied by removing the release liner, positioning the bandage over the wound and placing the adhesive onto the skin of the person. Such prepackaged adhesive bandages are known as Band-Aids®.

Adhesive bandages are typically individually pre-packaged and because of this are available only in predetermined sizes. Numerous dispensing devices are known for dispensing the pre-packaged adhesive bandages. One such dispensing device is disclosed in U.S. Pat. No. 8,851,284 which disclosed an adhesive bandage dispensing arrangement which includes prepackaged adhesive bandages attached to a single roll. This patent also discloses an elongated bandage strip which comprises a continuous substrate coated with an adhesive to which a continuous gauze strip is adhered. A release liner covers the substrate and is coextensive with it in a direction transverse to the longitudinal direction of the strip. The release liner protects the gauze strip from contamination. Other elongated bandage strips are disclosed in U.S. Pat. Nos. 5,843,011 and 6,362,288. These patents disclose self-adhesive bandage rolls. While suitable for their intended purpose, these disclosed rolls lack the ability to seal all around a wound thereby securing the wound dressing sufficiently around the wound while also preventing infection from possibly arising due to the wound not being enclosed from the ambient environment.

Accordingly, there is a need for a continuous self-adhesive bandage roll which may be utilized for dispensing a self-adhesive bandage which may be of a desirable length for covering a wound of a predetermined length while providing an adhesive portion enclosing a gauze portion for securing the self-adhesive bandage to a person while completely surrounding the wound.

SUMMARY OF THE INVENTION

In a first embodiment, a bandage includes a body having a predetermined length and width defined by side edges. The body having an outer surface and an internal surface and includes a central axis. The internal surface of the body carries an adhesive. An attachment portion is defined by adhesive designated for exposure. A first removable dressing component having a predetermined length and width is carried by the adhesive disposed over the central axis of the body. A second removable dressing component having a predetermined length and width is carried by the adhesive disposed over the central axis of said body. The second removable dressing component being adjacent to the first removable dressing component along the central axis. The respective widths of the first and second removable dressing components being less than the width of the body enabling a side edge attachment portion to be defined proximate the side edges of the body wherein the removal of the first removable dressing component exposes the adhesive defining an end attachment portion of the bandage.

In a second embodiment, a bandage includes a body having a predetermined length and width defined by side edges. The body has an outer surface and an internal surface and a central axis. A pressure sensitive adhesive is carried by the internal surface of the body. An attachment portion is defined by adhesive designated for exposure. A first removable dressing component having a predetermined length and width is carried by the adhesive disposed over the central axis of the body. A second removable dressing component having a predetermined length and width is adjacent to the first removable dressing component along said central axis. A third removable dressing component having a predetermined length and width is carried by the adhesive disposed over the central axis of the body. The respective widths of the first, second and third removable dressing components being less than said width of the body enabling a side edge attachment portion to be defined proximate the side edges of the body. A weak boundary layer is formed between the first and third removable dressing components and the adhesive wherein the position of the first removable dressing component is fixed without being bonded to the body. The bandage is a continuous bandage of a predetermined length greater than five inches and may be dispensed to any length equal to the entire length of the roll. Wherein the bandage may transpose to an adhesive bandage for application to a wound by having the first and third removable dressing components removed exposing the adhesive and defining a first edge attachment portion and a second edge attachment portion which in conjunction with the side edge attachment portion surround the second removable dressing component.

A third embodiment includes a method of manufacturing an adhesive bandage. The method includes providing a base substrate having a central axis with the base substrate having a predetermined width and length. A pressure sensitive adhesive is applied to the base substrate. A dressing component is applied to at least a portion of the pressure sensitive adhesive such that a weak boundary layer is established between the dressing component and the pressure sensitive adhesive and enabling for the removal of certain portions of the dressing component from the adhesive exposing the adhesive previously covered by the respective dressing component portion to define attachment portions for attaching the bandage to an object.

BRIEF DESCRIPTION OF THE DRAWINGS

The subject matter which is regarded as the invention is particularly pointed out and distinctly claimed in the claims after the specification. The foregoing and other features, and advantages of the invention are apparent from the following detailed description taken in conjunction with the accompanying drawings in which:

DETAILED DESCRIPTION

The present invention can be understood more readily by reference to the following detailed description, examples, drawings, and claims, and their previous and following description. However, before the present devices, systems, and/or methods are disclosed and described, it is to be understood that this invention is not limited to the specific devices, systems, and/or methods disclosed unless otherwise specified as such can, of course, vary. It is also to be understood that the terminology used herein is for describing aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention.

Figure 1A:
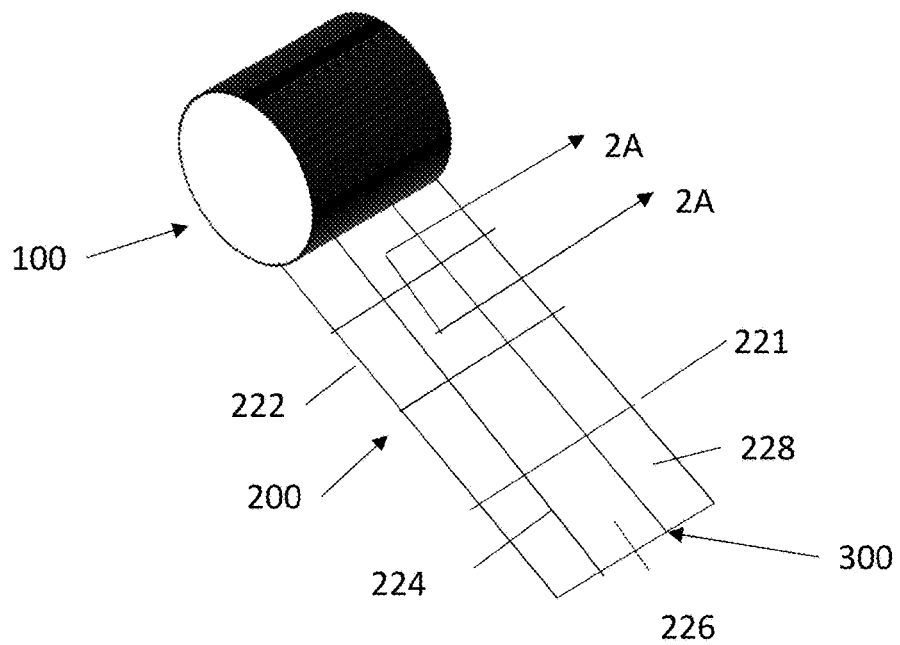
FIG. 1A illustrates a perspective view of an adhesive bandage according to the present invention.
Figure 1B:
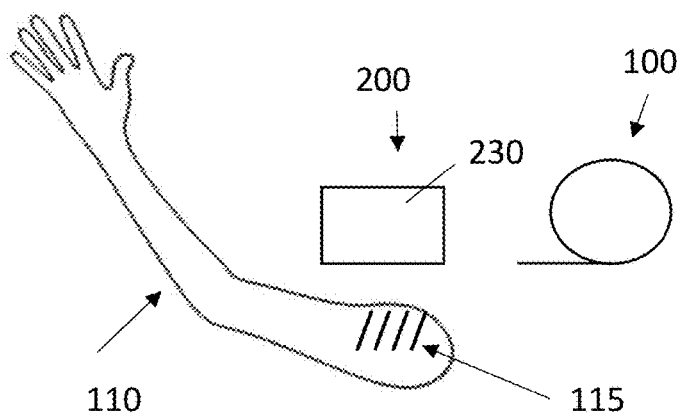
FIG. 1B illustrates an environment for utilization of an adhesive bandage according to the present invention.

As illustrated in FIGS. 1A and 1B a bandage roll 100 of an adhesive bandage is unrolled to display a bandage portion 200 for subsequent application to a wound. The adhesive bandage has a length when unrolled at least five inches in length. Preferably the bandage roll is two feet in length when unrolled. The important aspect of the invention is that the end user may determine the length of the adhesive bandage to be applied to the wound. For a roll which is two feet in length, multiple bandages of different lengths may be produced. The roll has a predetermined width defining side edges 221 with a central axis 226. The bandage portion 200 includes an internal surface 222 and external surface 230. The adhesive bandage includes an adhesive 224 carried by the internal surface 222 to define an attachment portion for attaching to an end user. A dressing component 300 preferably extends along the length of the body along the central axis 226. The dressing component extends throughout the entire length of the exposed bandage body for providing coverage over a wound. In the preferred embodiment, dressing component 300 is comprised of individual dressing segments which are laid side by side along the entire length of the bandage roll. Preferably perforations 228 are formed along the entire width of bandage 222 including the edges formed alongside the individual dressing segments. This enables the bandage to be sized by merely tearing the bandage portion 200 along one of the respective perforations.

As shown in FIG. 1B, a bandage portion 200 may be separated from bandage roll 100 to define an adhesive bandage for application to a wound. As shown in FIG. 1B, an arm 110 includes a wound 115 of a predetermined area. Bandage portion 200 may be cut to a length desired to accommodate coverage of the wound of the predetermined area. The ability to construct a bandage of a desired length from the roll 100 is an important aspect of the invention.

Figure 2A:
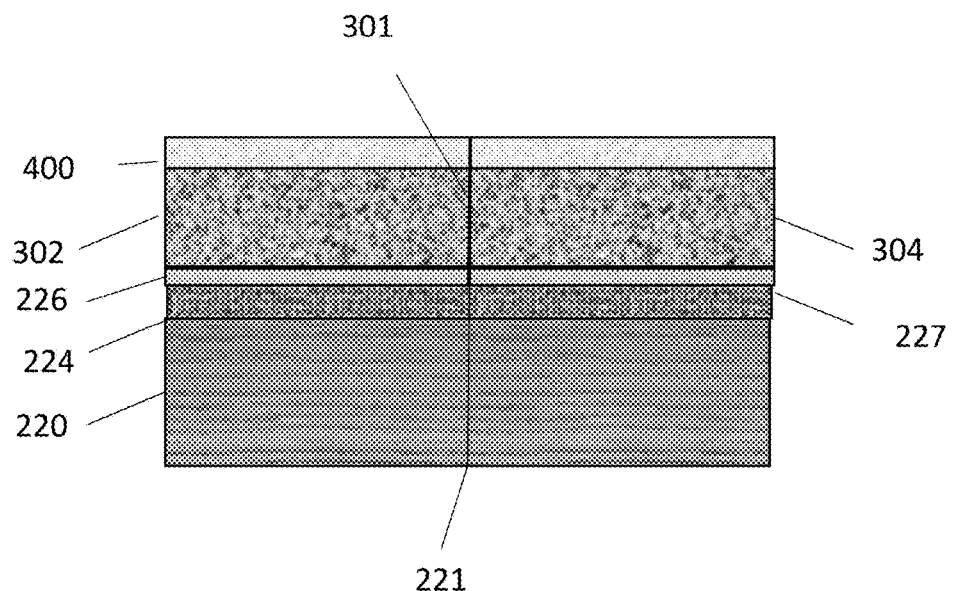
FIG. 2A illustrates a cross-section of an adhesive bandage taken along line 2A of FIG. 1A.

FIG. 2A is a cross-section taken from line 2A-2A of FIG. 1A. The cross-section identifies components of bandage 200. The initial layer is body layer 220. Body layer 220 may comprise a hydrophilic polyurethane having a water uptake of twenty-five percent. Alternatively, the body layer may comprise materials which are conventionally employed to form thin film surgical dressings. Particularly apt materials are polyurethanes for example polyester or polyether polyurethanes known under the name ESTANE (Trademark) and polyether polyamides for example those known under the name PEBAX (Trademark). Preferably the body layer is moisture vapor permeable and has a moisture vapor transmission rate of at least 300 $gm^2$ per twenty-four hours. Preferably the body layer has a thickness from fifteen to eighty μm.

Adjacent body layer 220 is adhesive layer 224. Adhesive layer 224 is preferably a pressure sensitive adhesive layer. Pressure sensitive adhesive is preferably formed from an adhesive which is conventionally used for contact with the skin. Most desirably, the pressure sensitive adhesive is an acrylic adhesive such as an acrylate ester copolymer adhesive formed by the copolymerization of 2-ethyl-hexyl acrylate, butyl and acrylic acid. The layer of adhesive provided on the body layer may be a continuous layer of moisture vapor permeable adhesive such as acrylate surgical. Alternatively, the layer of adhesive may be a discontinuous layer of adhesive spread over the body layer 220.

As shown in FIG. 2A a first removable dressing component 302 and a second removable dressing component 304 are carried by body layer 220. Preferably first removable dressing component 302 and second removable dressing component 304 are individual pieces positioned on adhesive layer 224 and preferably abut each other at plane 301. In the configuration shown in FIG. 2A a thin plastic film 226 is integral with the first and second removable dressing components. In this configuration a weak boundary layer 227 is formed between the thin plastic film 226 and adhesive layer 224. The weak boundary layer is a non-adhesive interface disassociation layer which enables for the removal of either the first or second removable dressing components 302 304 from adhesive layer 224 and respectively body layer 220 exposing adhesive layer 224 for subsequent attachment to a wound site. Consequently, first and second removable dressing components 302 304 have a low stripping load such that the removable dressing components may be removed from the adhesive layer 227 without damaging the integrity of the adhesive layer 227 enabling the adhesive layer to be utilized for attachment to a wound site. Additionally, a removable protector layer 400 is disposed over the removable dressing components for providing sterility. The removable protector layer 400 may be distinct pieces associated with a distinct dressing component individually. Preferably, removable protector layer 400 is silicone coated release paper and has a low stripping load such that the release paper may be removed from the adhesive layer 227 without damaging the integrity of the adhesive layer 227. In the preferred embodiment, perforation 221 is aligned with plane 301 enabling an entire section of bandage 200 to be removed cleanly without any tearing of the bandage roll.

Figure 2B:
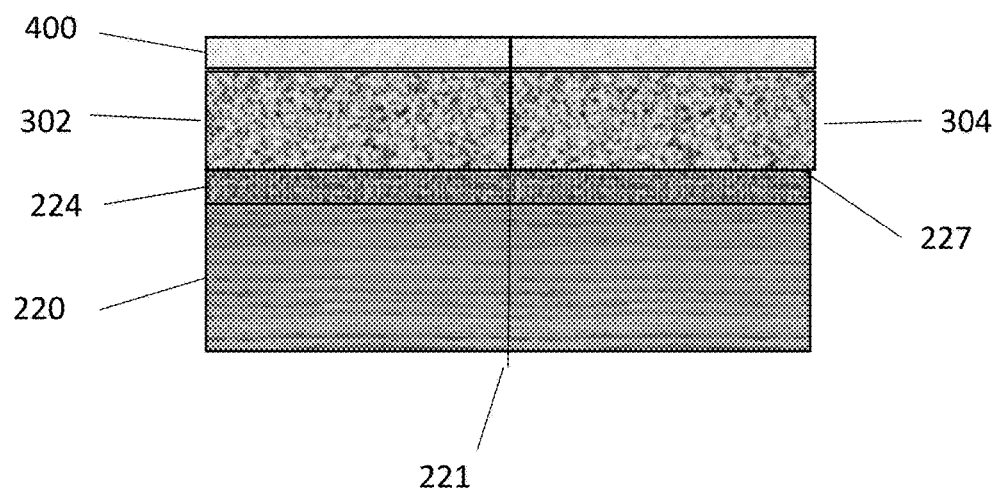
FIG. 2B illustrates an alternative embodiment cross section of an adhesive bandage according to the present invention.

As shown in FIG. 2B, an alternative configuration of the bandage may be had. In this configuration a weak boundary layer 227 exists directly between the respective dressing components 302 and 304 and adhesive layer 224. This weak boundary layer may be had by applying a lubricant to the surface of the removable dressing components. Additionally, the adhesive properties of the pressure adhesive may not be sufficient to firmly interface with the respective removable dressing components to bond the removable dressing components with the adhesive layer 227 until pressure is applied to the bandage.

Figure 3A:
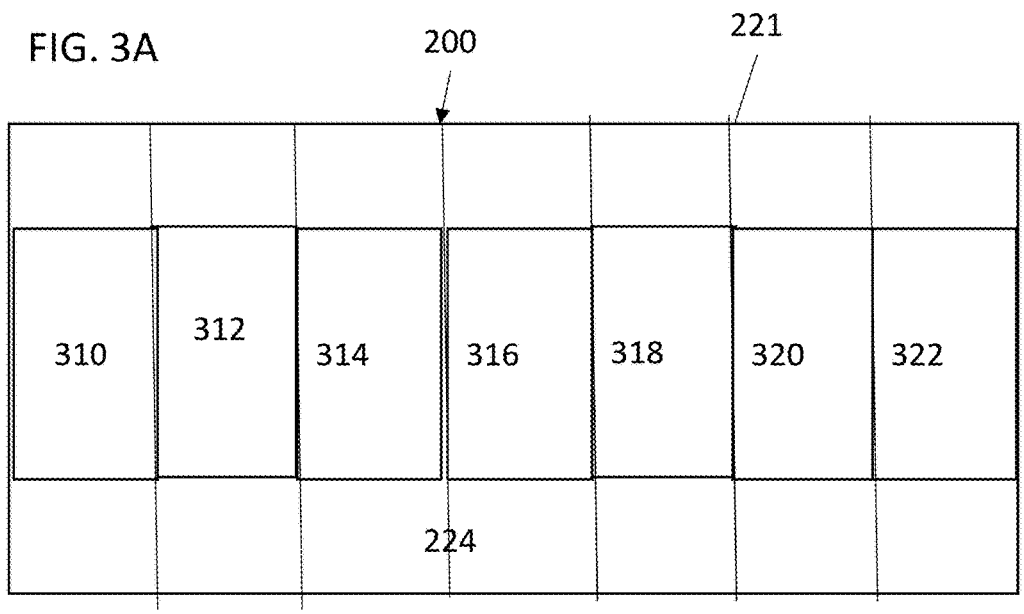
FIG. 3A illustrates an adhesive bandage according to the present invention.
Figure 3B:
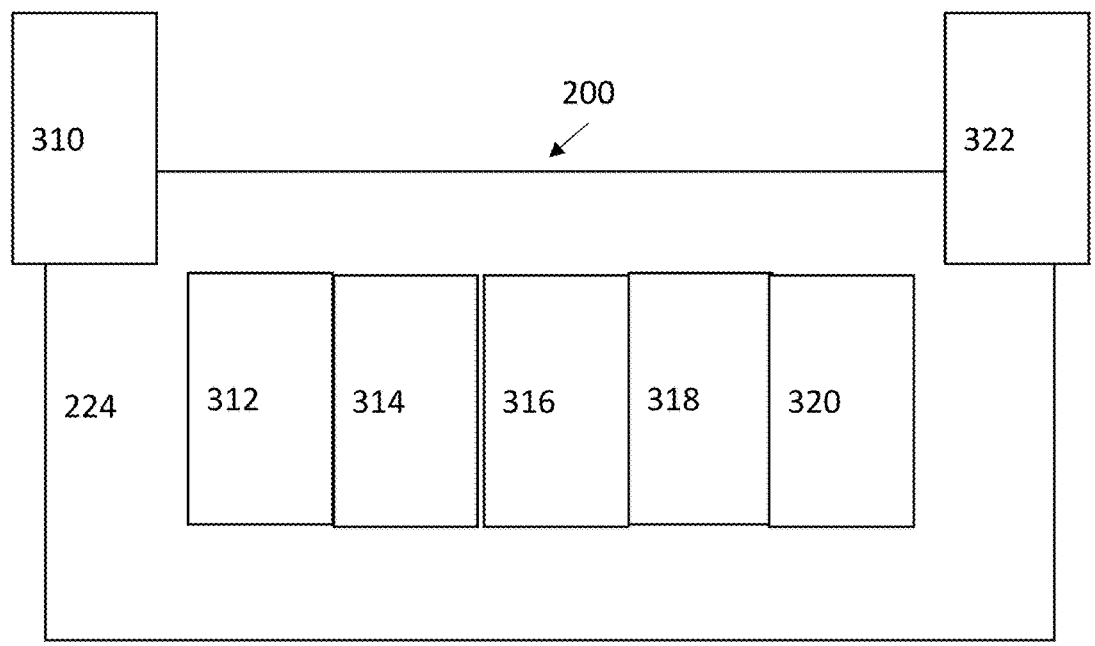
FIG. 3B illustrates the removal of certain central dressing components of an adhesive bandage according to the present invention.

FIGS. 3A and 3B illustrate an important aspect of the invention. As shown in FIG. 3A, a plurality of removeable dressing components 310-322 are displayed. Each removeable dressing component may be removed while maintaining the integrity of the underlying adhesive layer 224. Preferably, each removable dressing component is an individual dressing component separate and distinct from each adjacent one. This will enable each component to be removed without difficulty. Originally as shown, bandage portion 200 is defined at a predetermined length to cover the wound as shown in FIG. 1B. Preferably, the body is perforated along the width which corresponds with the edge of a respective dressing component. The removable dressing components 310-322 have a predetermined length and width and are disposed over the central axis of the bandage body. The respective widths of the removable dressing components are less than the width of the body enabling a side edge attachment portion 240 which is a portion of adhesive layer 224. When initially cut from the roll, the entire length of the bandage body preferably includes removable dressing components. In the preferred embodiment, the respective dressing components are a sterilized cotton gauze. Other dressing components known in the art may be utilized. The respective dressing components may be singularly attached to the adhesive bandage. In an additional embodiment, the dressing component may consist of a single layer of cotton gauze which has been sectionalized into the respective dressing components by perforating the respective sections enabling the respective removable dressing components to be individually selectable for removal. As shown in FIG. 3B, a removable dressing component 310 is removed exposing underlying adhesive 224, this is an important aspect of the invention. By removing a removable dressing component, a first edge attachment portion 244 is established which may be used to secure an edge portion of the bandage to a wound site. Also, as shown in FIG. 3B, a second removable dressing component 322 is removed exposing underlying adhesive 224 to form a second edge attachment portion 246.

Figure 4A:
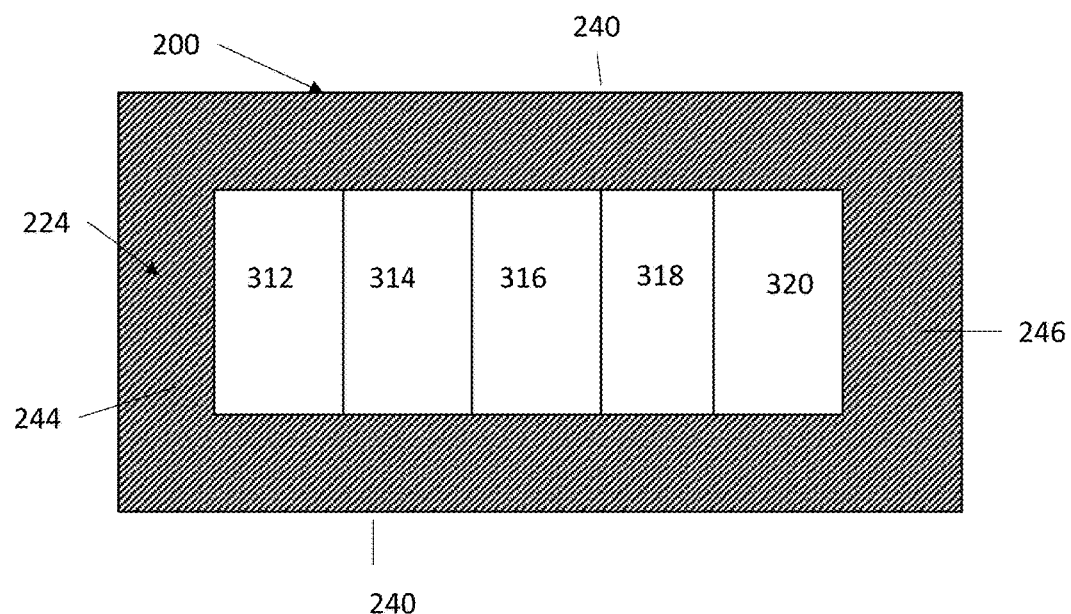
FIG. 4A illustrates an adhesive bandage with the removal of certain central dressing components for application according to the present invention.
Figure 4B:
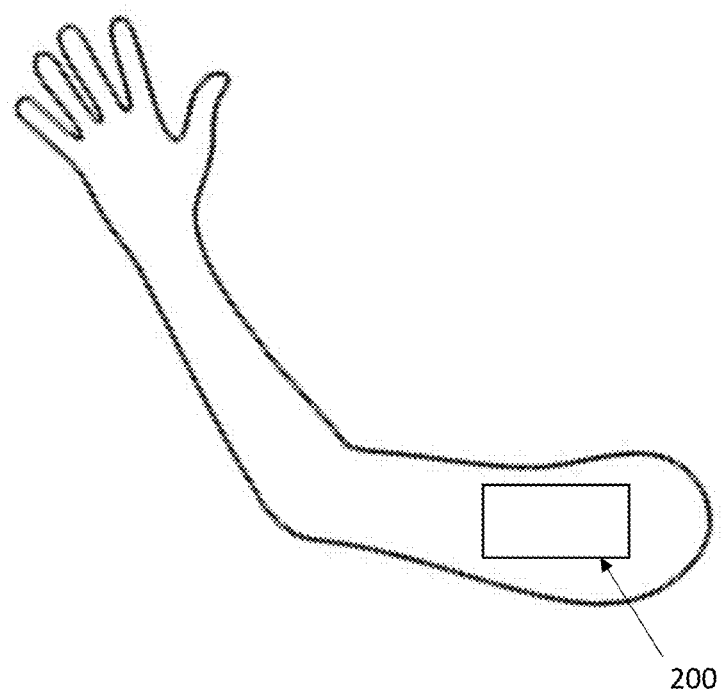
FIG. 4B illustrates the application of an adhesive bandage according to the present invention.

As shown in FIGS. 3B, 4A and 4B, the ability to remove removable dressing components enables a bandage to be constructed specifically for the wound site needed to be covered. By determining the length of the bandage necessary, the respective bandage length may be separated from a roll. As the removable dressing sections extend along the entire length of the bandage body, the necessary size of coverage of the wound may be determined. With the ability to remove the central dressing sections, the adhesive layers near the front and rear edges may be exposed enabling the entire adhesive attachment portions to surround the central dressing sections enabling three hundred and sixty degrees of attachment of the bandage to the wound site. The full three hundred and sixty-degree adhesive exposure provides for a secure fit of the bandage to the wound site as shown in FIG. 4B providing for a sterile healing environment.

Figure 5:
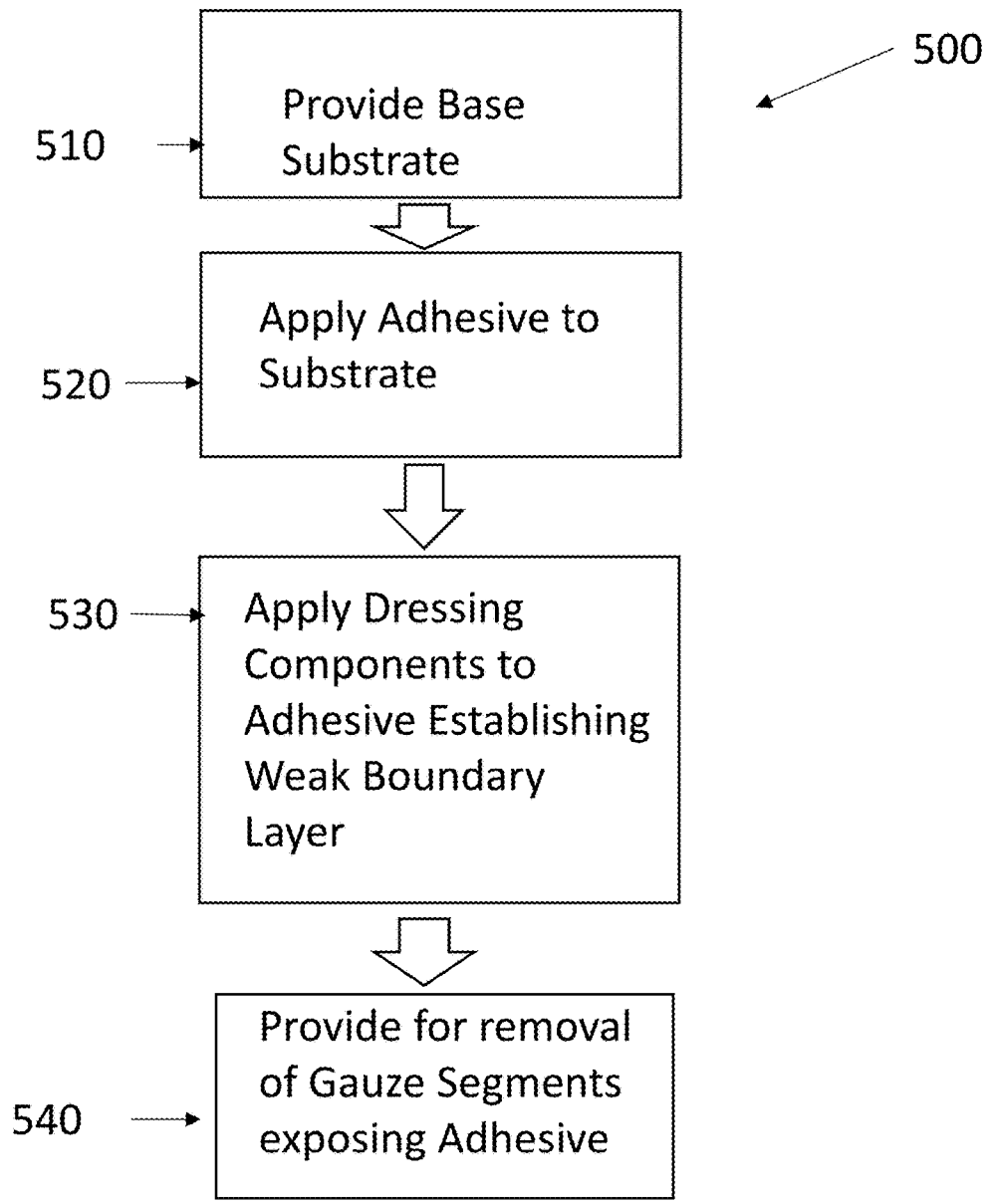
FIG. 5 illustrates a method of manufacturing an adhesive bandage according to the present invention.

FIG. 5 illustrates a method 500 for manufacturing an adhesive bandage according to the present invention. Initially at step 510 a base substrate is provided to defining the bandage body. An adhesive, preferably a pressure sensitive adhesive is applied to the base substrate at step 520. At step 530, a gauze segment is applied to the adhesive layer in a manner such that a weak boundary layer is defined between the adhesive layer and respective gauze segment. The weak boundary layer is such that the respective gauze segment may be removed from the adhesive layer in a manner wherein the adhesive layer maintains its structural integrity for being utilized as an attachment portion for being affixed to a person's skin. At step 540 the gauze segment is manipulated to provide for the removal of the gauze segment for exposing the adhesive. In the preferred embodiment, this step includes perforating sections of the gauze enabling respective sections to be removed while maintaining adjacent gauze sections on the base substrate. In an alternative embodiment providing may include defining separate gauze components and individually positioning the individual gauze components onto the base substrate with a weak boundary layer formed between each respective gauze component and adhesive layer.

Thus, it may be seen that a more advantageous design for an adhesive bandage may be had according to the present invention. A common problem with adhesive bandages is that they come prepackaged in sterile packages with a predetermined size. Such sizes may not be sufficient or over compensate for a wound site. The invention provides for a configurable adhesive bandage which may be configured by a user to accommodate the respective wound. Unlike prior art adhesive bandages which consist of a single roll which may be unfurled, such prior art does not provide for secure and sterile attachment of an adhesive bandage to the wound site. The present invention provides for a secure and sterile environment by enabling the removal of central gauze components which thereby expose the underlying adhesive layer in a manner which enables the entire periphery of the bandage, side, and end edges, to be secured to the wound site. In operation an individual may extend the bandage from the roll to the length which covers the wound and provides for a secure attachment portion around the wound site. This additional securing portion provided by the present invention provides for a more sterile environment and a more secure attachment as the entire edges are held in place to the wound site preventing the bandage from having any loose edges. This bandage may also be utilized in surgical environments.

I claim:

1. A bandage comprising:
   a body having a predetermined length and width defined by side edges, said body having an outer surface and an internal surface, said body having a central axis;
   an adhesive carried by said internal surface of said body:
   an attachment portion defined by adhesive designated for exposure;
   a dressing component for covering a wound extending lengthwise along the central axis of said body, said dressing component comprised of at least a first, second and third dressing segment wherein each segment is adapted for covering a wound or being removed, said first, second and third dressing segments aligned along said central axis;
   a width of said first dressing segment and a width of said third dressing segment being less than said width of said body enabling a side edge attachment portion to be defined proximate the side edges of said body; and wherein said first and third dressing segments may be removed exposing said adhesive defining an end attachment portion of said bandage enabling said second dressing segment to cover a wound and be maintained in position over a wound.

2. The bandage of claim 1 wherein a weak boundary layer is formed between said first dressing segment and said adhesive wherein the first dressing segment is fixed without being bonded to the body.

3. The bandage of claim 2 including a thin plastic film disposed between said first dressing segment and said adhesive defining said weak boundary layer.

4. The bandage of claim 2 including a lubricant disposed between said first dressing segment and said adhesive defining said weak boundary layer.

5. The bandage of claim 1 wherein said adhesive is a pressure sensitive adhesive.

6. The bandage of claim 5 wherein said second dressing segment is adhered to said body by said pressure sensitive adhesive when pressure is applied to said pressure sensitive adhesive.

7. The bandage claim 1 wherein said bandage is a continuous bandage of a predetermined length formed into a roll and may be dispensed to any length equal to an entire length of said roll.

8. The bandage of claim 7 wherein said bandage has a length at least equal to five inches when unrolled.

9. The bandage of claim 1 transposing to an adhesive bandage for application to a wound by having said first and third dressing segments removed exposing said adhesive and defining a first end attachment portion and a second end attachment portion which in conjunction with said side edge attachment portion surround said second dressing segment.

10. The bandage of claim 1 including a removable protector layer oppositely disposed from said outer surface of said body and carried by said attachment portion and covering said attachment portion and said first and second dressing segments.

11. A bandage comprising:

a body having a predetermined length and width defined by side edges, said body having an outer surface and an internal surface, said body having a central axis;

a pressure sensitive adhesive carried by said internal surface of said body, an attachment portion defined by adhesive designated for exposure;

a dressing component for covering a wound extending lengthwise along the central axis of said body, said dressing component comprised of at least a first, second and third dressing segment wherein each segment is adapted for covering a wound or being removed, said first, second and third dressing segments aligned along said central axis;

said first, second and third dressing segments each having a width being less than said width of said body enabling a side edge attachment portion to be defined proximate the side edges of said body;

a weak boundary layer formed between said first dressing segment and said adhesive wherein the first dressing segment is fixed without being bonded to the body;

a weak boundary layer formed between said third dressing segment and said adhesive wherein the third dressing segment is fixed without being bonded to the body;

said bandage is a continuous bandage of a predetermined length greater than five inches; and wherein the bandage may transpose to an adhesive bandage for application to a wound by having said first and third dressing segments removed exposing said adhesive and defining a first end attachment portion and a second end attachment portion which in conjunction with said side edge attachment portion surround said second dressing segment enabling said second dressing segment to cover a wound and be maintained in position over a wound.

12. The bandage of claim 11 including a thin plastic film disposed between said first dressing segment and said adhesive defining said weak boundary layer.

13. The bandage of claim 11 including a lubricant disposed between said first dressing segment and said adhesive defining said weak boundary layer.

14. The bandage of claim 11 including a removable protector layer oppositely disposed from said outer surface of said body and carried by said attachment portion and covering said attachment portion and said first, second and third dressing segments.

15. The bandage of claim 11 wherein said first, second and third dressing segments are formed from a single dressing web and are defined by perforations being defined within the single dressing web enabling said first and third dressing segments to be removed from said pressure sensitive adhesive layer along said respective perforations.

16. A method of manufacturing an adhesive bandage comprising:

providing a base substrate having a central axis, said base substrate having a predetermined width and length;

applying a pressure sensitive adhesive to said base substrate;

applying a dressing component to at least a portion of said pressure sensitive adhesive such that a weak boundary layer is established between said dressing component and said pressure sensitive adhesive;

said dressing component for covering a wound extending lengthwise along the central axis of said base substrate, said dressing component comprised of at least a first, second and third dressing segment wherein each segment is adapted for covering a wound or being removed, said first, second and third dressing segments aligned along said central axis; and enabling removal of certain dressing segments of said dressing component from said adhesive exposing said adhesive previously covered by said respective dressing segment to define attachment portions for attaching said bandage to an object enabling a respective dressing segment to cover a wound.

17. The method of claim 16 wherein said dressing component is perforated into separate dressing segments enabling certain dressing segments to be removed from said adhesive along said perforations exposing said adhesive for contact while maintaining other dressing segments of said dressing component with said adhesive.

18. The method of claim 16 wherein said adhesive bandage includes a thin plastic film for defining said weak boundary layer.

19. The method of claim 16 wherein said applying a dressing component includes positioning individual dressing segments side by side along the length of said base substrate.

* * * * *